(12) United States Patent
Zakashefski

(10) Patent No.: US 11,013,334 B2
(45) Date of Patent: May 25, 2021

(54) HEAD SUPPORT DEVICE

(71) Applicant: Nick Zakashefski, Branchburg, NJ (US)

(72) Inventor: Nick Zakashefski, Branchburg, NJ (US)

( * ) Notice: Subject to any disclaimer, the term of this patent is extended or adjusted under 35 U.S.C. 154(b) by 0 days.

(21) Appl. No.: 16/841,123

(22) Filed: Apr. 6, 2020

(65) Prior Publication Data
US 2020/0315359 A1 Oct. 8, 2020

Related U.S. Application Data

(60) Provisional application No. 62/830,214, filed on Apr. 5, 2019.

(51) Int. Cl.
| | |
|---|---|
| *A47C 16/00* | (2006.01) |
| *A61M 21/02* | (2006.01) |
| *A62B 23/02* | (2006.01) |
| *H04R 1/02* | (2006.01) |
| *H04R 3/00* | (2006.01) |
| *F16M 13/04* | (2006.01) |
| *A61M 21/00* | (2006.01) |

(52) U.S. Cl.
CPC .............. *A47C 16/00* (2013.01); *A61M 21/02* (2013.01); *A62B 23/025* (2013.01); *F16M 13/04* (2013.01); *H04R 1/028* (2013.01); *H04R 3/00* (2013.01); *A61M 2021/0016* (2013.01); *H04R 2420/07* (2013.01)

(58) Field of Classification Search
CPC ........... A47C 16/00; A47C 7/36; A47C 7/383; A61M 21/02; A61M 2021/0016; A62B 23/025; H04R 1/028; H04R 3/00; H04R 2420/07; A61F 9/04; F16M 13/04
USPC .............................. 248/118; 5/636, 645, 646
See application file for complete search history.

(56) References Cited

U.S. PATENT DOCUMENTS

| | | | | |
|---|---|---|---|---|
| 1,916,507 | A * | 7/1933 | Green ................. | A41D 25/001 2/91 |
| 4,872,217 | A * | 10/1989 | Kitayama ................. | A61F 9/04 2/15 |
| 8,205,283 | B1 * | 6/2012 | Russell .................. | A47C 7/383 5/636 |
| 8,256,049 | B1 * | 9/2012 | Sinks ...................... | A47C 16/00 5/632 |
| 2005/0015851 | A1 * | 1/2005 | Kaufman ................. | A61F 9/04 2/208 |

(Continued)

*Primary Examiner* — Christopher Garft
(74) *Attorney, Agent, or Firm* — David R. Conklin; Kirton McConkie

(57) ABSTRACT

A head support device having two handles or receptacles connected by a support strap, wherein the handles or receptacles are configured to support or accommodate the user's hands, and the support strap is configured to support or accommodate a portion of the user's head, namely, the user's face. In use, the user wears or otherwise passively contacts the handles or receptacles of the device such that the support strap maintains a desired distance between the user's hands. When in the seated position, the user contacts the support strap with their face, such that the user's hands and the handles or receptacles contact opposite sides of the user's head. The user further supports their arms by placing their elbows on their knees, upper legs, or other stable surface, thereby transferring the weight of their head to a stable surface via their forearms.

10 Claims, 14 Drawing Sheets

(56) References Cited

U.S. PATENT DOCUMENTS

| | | | | |
|---|---|---|---|---|
| 2009/0255026 A1* | 10/2009 | Benner | ............... | A61F 9/04 |
| | | | | 2/12 |
| 2010/0213327 A1* | 8/2010 | Ochs-Sobczak | ..... | A41D 13/081 |
| | | | | 248/118 |
| 2011/0257713 A1* | 10/2011 | Clegg | ............ | A61M 21/02 |
| | | | | 607/90 |
| 2017/0209309 A1* | 7/2017 | Lazor | ................ | A61F 9/04 |
| 2017/0264994 A1* | 9/2017 | Gordon | ............ | H04R 1/026 |
| 2018/0242747 A1* | 8/2018 | Berube | ............ | A47C 16/00 |
| 2019/0343307 A1* | 11/2019 | Cullins | ............ | A47G 9/1036 |

\* cited by examiner

HEAD SUPPORT DEVICE

RELATED APPLICATIONS

This application claims priority to U.S. Provisional Patent Application Ser. No. 62/830,214, filed Apr. 5, 2019, which is incorporated herein in its entirety.

FIELD OF THE INVENTION

The present invention relates generally to a device for use in supporting a user's head when in a seated position. In particular, the present invention relates to a sling device having two handles or receptacles connected by a support strap, wherein the handles or receptacles are configured to support or accommodate the user's hands, and the support strap is configured to support or accommodate a portion of the user's head, namely, the user's face. In use, the user wears or otherwise passively contacts the handles or receptacles of the device such that the support strap maintains a desired distance between the handles. When in the seated position, the user contacts the support strap with their face, such that the user's hands and the handles or receptacles contact opposite sides of the user's head. The user further supports their arms by placing their elbows on their knees, upper legs, or other stable surface, thereby transferring the weight of their head to the surface via their forearms.

BACKGROUND OF THE INVENTION

Sleep deprivation, also known as insufficient sleep, is the condition of not having enough sleep. It can be either chronic or acute and may vary widely in severity. A chronic sleep-restricted state can cause fatigue, daytime sleepiness, clumsiness, and weight loss or weight gain. In some instances, sleep deprivation can adversely affect brain and cognitive function. The dangers of sleep deprivation while driving are apparent and are known to produce some of the same hazardous effects as being intoxicated. Sleep deprivation commonly occurs as the result of insomnia, habitual use of stimulant drugs, sleep apnea, travel, and social, career, or educational activities that displace sleep time (such as gaming, socializing with friends, long work hours, studying, or binge-watching media content). Visual signs of sleep deprivation may include head-nodding, lane drifting, and daydreaming, as well as inappropriate emotional and behavioral responses due to distorted perceptions. In many instances, sleep-deprived individuals may be seen dozing in public, often in uncomfortable or unconventional positions that become unstable once the individual drifts into sleep. One such sleeping position is a seated, hunched over sleeping position, as shown in FIG. 1. The PRIOR ART sleeping position demonstrated in FIG. 1 requires the user to maintain sufficient consciousness and muscle control in order to hold up the user's head. Once the user loses consciousness, their sleeping position fails and they are abruptly awakened, which may be embarrassing and further contribute to their sleep-deprived condition.

Therefore, there exists an unmet need for a sleep aid device for assisting sleep-deprived individuals in safely, comfortably and stably sleeping in non-conventional sleeping positions. The present invention provides such a device.

BRIEF SUMMARY OF THE INVENTION

The present invention relates generally to a device for use in supporting a user's head when in a seated position. In particular, the present invention relates to a sling device having two handles or receptacles connected by a support strap, wherein the handles or receptacles are configured to support or accommodate at least a portion of the user's hands, and the support strap is configured to support or accommodate a portion of the user's head, namely, the user's face. In use, the user wears or otherwise passively contacts the handles or receptacles of the device such that the support strap maintains a desired distance between the user's hands. When in the seated position, the user contacts the support strap with their face, such that the user's hands and the handles or receptacles contact opposite sides of the user's head. The user further supports their arms by placing their elbows on their knees, upper legs, or other stable surface, thereby transferring the weight of their head to a stable surface via their forearms.

Any of the features described herein may be combined in order to arrive at a desired configuration in accordance with the explicitly stated and intended operation of the present invention. Use herein of the transitional phrases "in some embodiments" and "in some instances" is not intended to limit the scope of any particular embodiment to a specific feature or set of features disclosed therewith. Rather, the intention of all the various embodiments described herein is to provide frameworks of context in which a specific feature or a set of features may be comprehended and understood in the context of the inventive concept as a whole. Accordingly, the entirety of the present disclosure is to be understood as a body of interchangeable and modular elements that may be selected and combined (in accordance with the requisite purview of one having ordinary skill in the art) to achieve a device, system, or method within the context of the inventive concept, as a whole, disclosed herein.

In a first aspect of the invention, The present invention uses material that slips onto both hands and supports the head and neck across the face or chin area. The hand portion of the product comprises an opening, and in some instances is shaped like mittens or finger gloves. The support area is connected at the wrists wide enough to hold the head in between. The material of the product may use an elastic material to expand to the different sizes and contours of the different hands and faces. Preferably the material is breathable for added comfort.

The product is used in the seated position by the user placing their elbows on the surface in front of them. They then insert each hand separately into the product hand receptacle on each side. The hands should be positioned so the palms are open against the side of the head, and the thumbs are pointing down. The user should then lean forward on the surface in front of them. In this position the center strap portion will cover the face completely allowing the individual to take a nap in darkness.

Other orientations allow the user to view entertainment or read. Again, the user must be in the seated position with elbows positioned on the surface in front of them. Each hand is inserted into the pockets. The thumbs should be pointing behind the user and the fingers should be pointing up with the palms open against the head. The center strap portion should be placed under the chin to support the head. This allows the user to look down or forward depending on the entertainment source. In some instances, the device of the present invention allows the user to place their elbows on the tops of their thighs.

Various embodiments of the head support device of the present invention allows the user to wear their own headphones while using the product. They simply place their hands over their headphones in the resting position. If the individual does not have headphones, various embodiments of the present invention comprise integrated headphones.

BRIEF DESCRIPTION OF THE DRAWINGS

It will be appreciated by those of ordinary skill in the art that the various drawings are for illustrative purposes only. The nature of the present invention, as well as other embodiments of the present invention, may be more clearly understood by reference to the following detailed description of the invention, to the appended claims, and to the several drawings.

FIGS. 5D and 5E show perspective side views of a user in a seated sleeping position, wherein FIG. 5D shows the user's hands interconnected via the head support device of FIGS. 5A-5C, and FIG. 5E shows a head support device with a hand aperture shaped like a glove.

DETAILED DESCRIPTION OF THE INVENTION

Figure 1:
FIG. 1 is a front view representation of a user in a seated, hunched-over position, wherein the user's head is held between the user's hands, and wherein the upright position of the user's head is maintained by placing and supporting the user's elbows on the user's knees, wherein said position demonstrates a PRIOR ART upright sleeping position.
Figure 2:
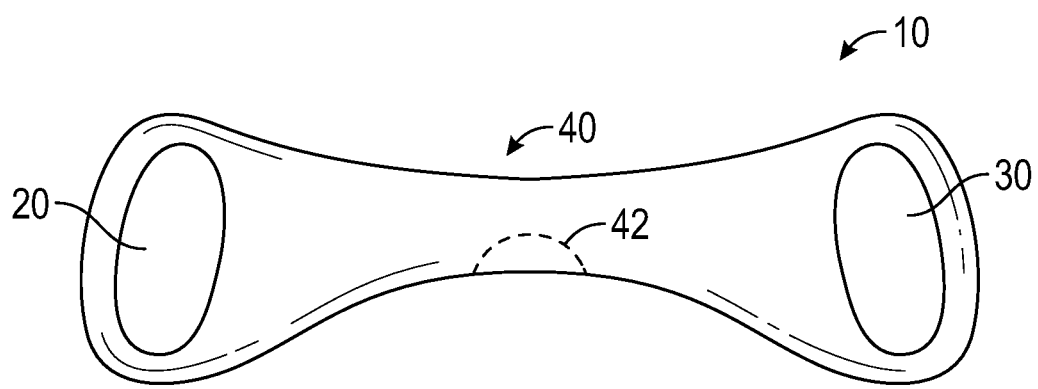
FIG. 2 is a front view of a head support device having hand apertures in accordance with a representative embodiment of the present invention.

Referring now to FIG. 2, a head support device 10 is shown. Head support device 10 comprises first and second hand apertures, 20 and 30. Hand apertures are located on opposite ends of device 10. In some embodiments, first and second hand apertures are each configured to receive at least one phalange of the user, for example, the index finger, the middle finger, the ring finger, or the pinky finger. In some embodiments, first and second hand apertures are each configured to receive the user's thumb. In some instances, hand apertures 20 and 30 each comprise a single aperture, as shown. In other embodiments, hand apertures 20 and 30 each comprise two or more sub-apertures, wherein each sub-aperture is configured to receive at least one phalange of the user. In some embodiments, hand apertures 20 and 30 are each configured to receive the user's entire hand, wherein the user inserts their entire hand through the respective aperture such that the aperture is positioned on the user's wrists or on the back of the user's hands.

Figure 3:
FIG. 3 is a front view representation of a user in the upright sleeping position of FIG. 1, wherein the user's hands are interconnected via the head support device of FIG. 2.
Figure 4:
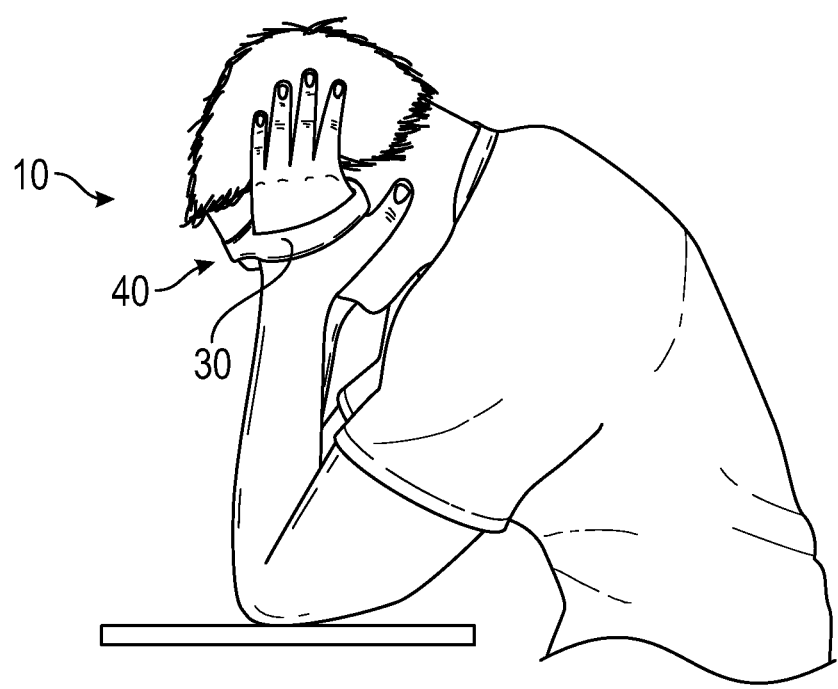
FIG. 4 is a perspective side view of a user in a seated sleeping position, wherein the user's hands are interconnected via the head support device of FIGS. 2 and 3.
Figure 5A:
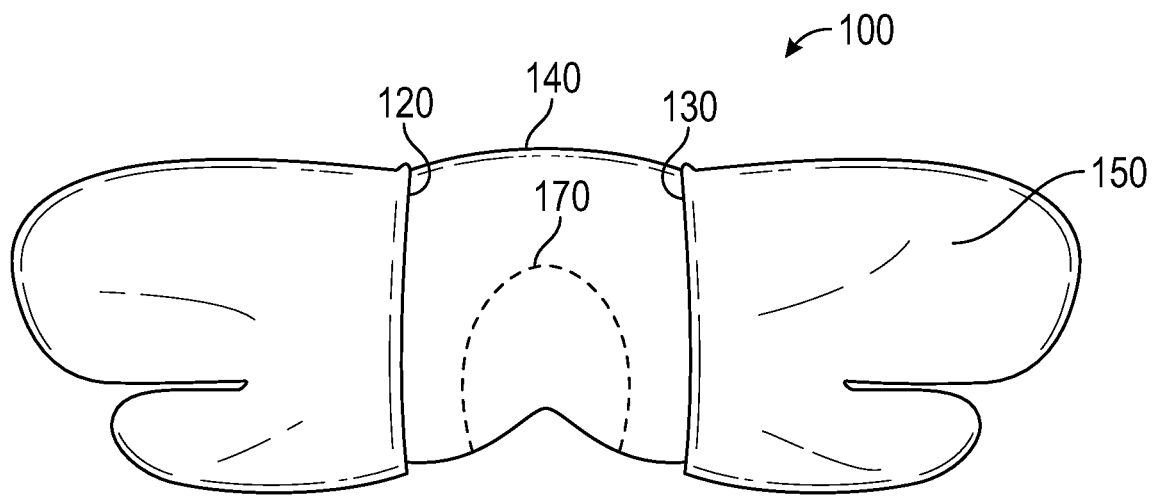
FIG. 5A is a front view of a head support device having left and right hand receptacles in accordance with a representative embodiment of the present invention.
Figure 5B:
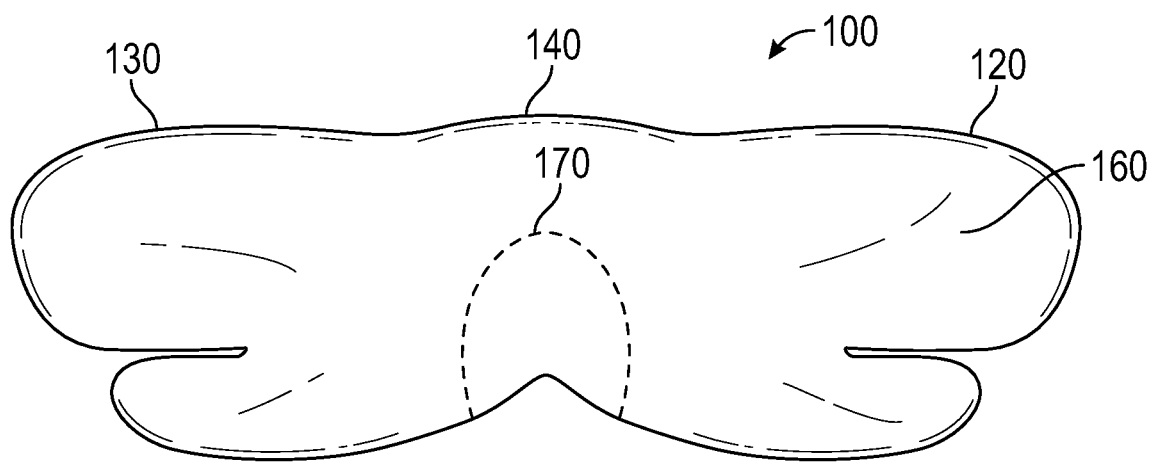
FIG. 5B is a rear view of the head support device of FIG. 5A.
Figure 5C:
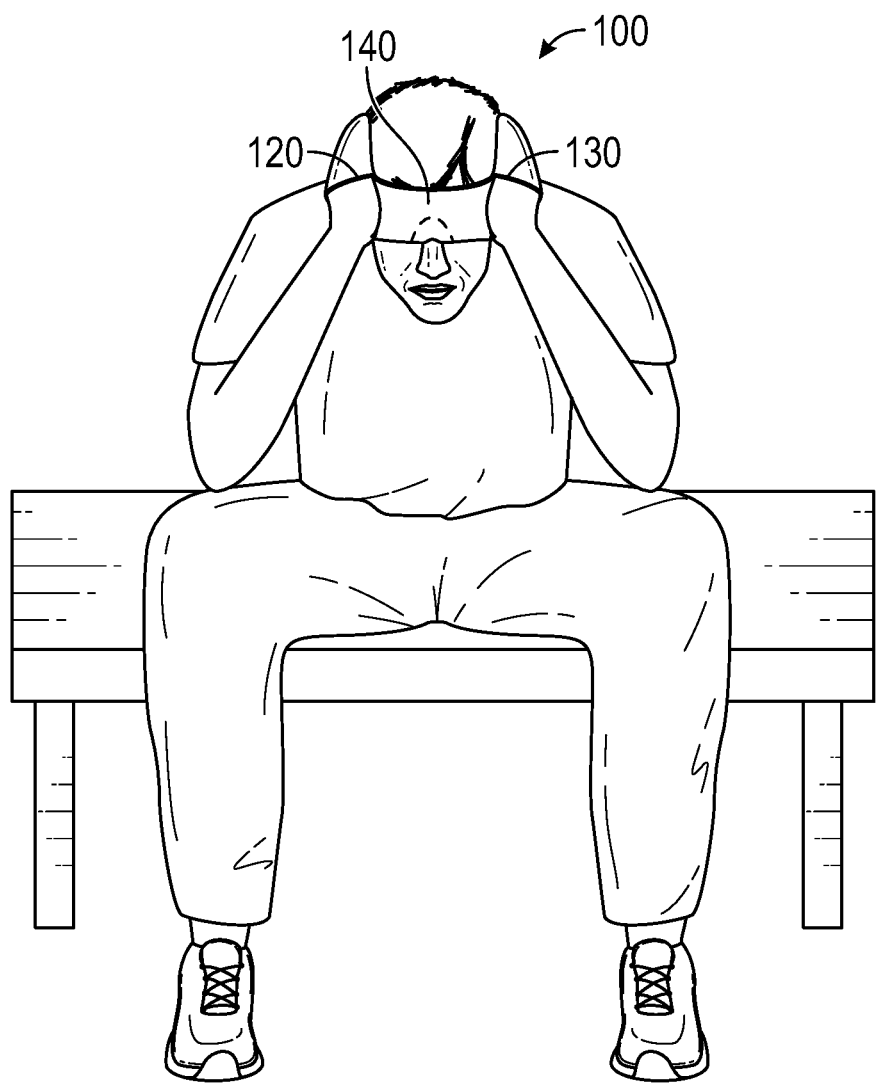
FIG. 5C is a front view representation of a user in the upright sleeping position of FIG. 1, wherein the user's hands are interconnected via the head support device of FIGS. 5A and 5B.
Figure 5D:
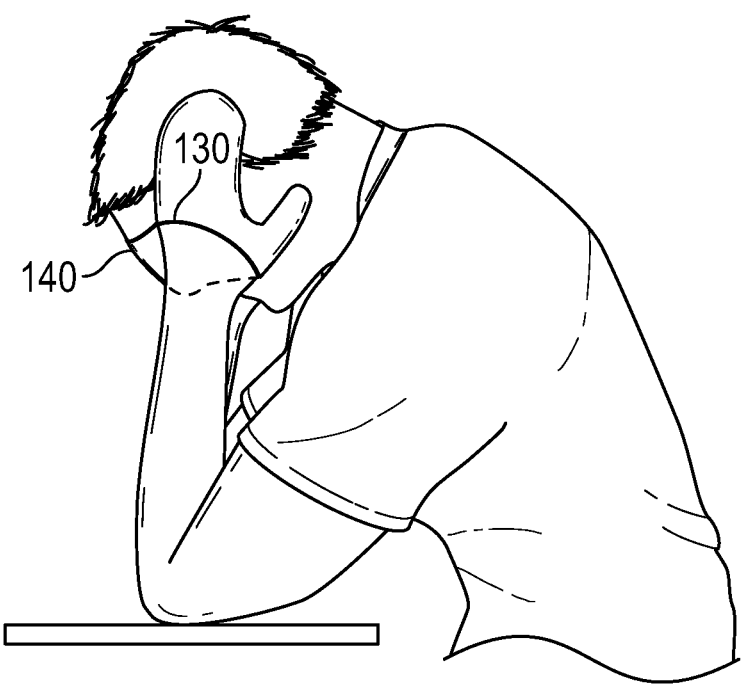
Figure 5E:
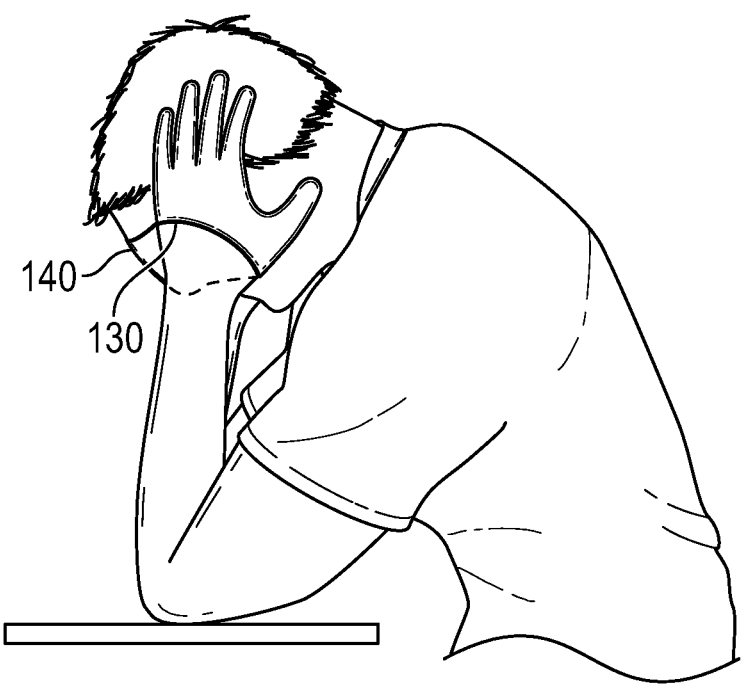

Head support device 10 further comprises a strap 40 that interconnected first and second hand apertures 20 and 30. Strap 40 is configured to contact a portion of the user's face. Strap 40 may comprise any dimensions compatible with the teachings of the present invention. In some embodiments, strap 40 comprises a length that is approximately equal to a width of the user's face. For example, in some embodiments strap 40 comprises a length of 3 inches, 4 inches, 5 inches, 6 inches, 7 inches or 8 inches. In some embodiments, the length of strap 40 is adjustable. When the user's phalanges, thumbs, and/or hands are inserted into the first and second hand apertures 20 and 30, strap 40 interconnects the user's hands, wherein strap 40 forms a sling against which the user may support their head when they grasp or contact opposite sides of their head with their hands, as shown in FIGS. 3 and 4. In some embodiments, head support device 10 may further comprise one or more ergonomic features or surfaces, such as a nose relief 42.

Head support device 10 may comprise any material that is compatible with the teaching of the present invention. In some embodiments, head support device 10 comprises a soft, pliable and/or elastic material that is comfortable for use against exposed skin. In one embodiment, device 10 comprises a neoprene material. In another embodiments, device 10 comprises a woven material. In another embodiment, device 10 comprises a non-woven material. Device 10 may further comprise various functional materials. For example, a functional material of the present invention may include a moisture-wicking material. A functional material of the present invention may further include a slip-resistant material. A functional material may further include a cooling or heating gel or other material that is inserted within, or otherwise associated with strap 40 or other surfaces of the device. A functional material may further include an elastomeric material.

The head support device of the present invention is generally used in conjunction with hands and arms to support the head on a stable surface, such as the user's knees, or a table surface. Referring now to FIGS. 5A-5E, a preferred embodiment of a head support device 100 is shown. In some embodiments, strap 140 comprises a thick elastic material or surface that is configured for placement across the face, wherein the material contours to the shape of the individual's facial features while supporting the head. In some embodiments, this surface is wide enough to cover the eye area and also distribute the weight of the head. First and second hand apertures 120 and 130 comprise pockets or receptacles to receive the user's hands. Pockets or receptacles may comprise any compatible shape, size or configuration. For example, pockets or receptacles may include a square, rectangular, circular, or irregular shape. In some embodiments, hand apertures 120 and 130 are shaped like a mitten (shown in FIGS. 5A-5D) or glove (shown in FIG. 5E), wherein pockets or compartments formed by apertures 120 and 130 have a backhand side 150 (shown in FIG. 5A) and a palm side 160 (shown in FIG. 5B). In some embodiments, the space between backhand side 150 and palm side 160 is open, such that backhand side 150 and palm side 160 are connected only around their respective perimeters. In some instances, apertures 120 and 130 further comprise internal dividers or partitions to separate at least some of the user's phalanges when inserted therein. In some instances, internal dividers or partitions form individual, internal pockets within apertures 120, 130.

When the user's hands are inserted within hand apertures 120 and 130, backhand side 150 is positioned on, or covers at least a portion of the back of the user's hand, and palm side 160 is positioned on, or covers at least a portion of the user's palm, wherein strap 140 extends between the user's palms and/or wrists to become a sling-like surface on which the user may rest their face. Strap 140 stably maintains the positions of the user's hands, such that the user may support their head without requiring consciousness or muscle control. Thus, combining the face support area and the apertures for hands allows the user to rest within the product. Accordingly, the elastic material used allows the product to stretch and accommodate the different size hands and heads of individual users. This same material also has thickness and depth to act as a cushion for the user.

In some embodiments, one or more surfaces of device 100 may comprise an ergonomic feature or element. For example, in some embodiments device 100 comprises a nose pocket 170. Nose pocket 170 generally comprises one or more features to accommodate the user's nose while resting their face against strap 140. In some embodiments, nose pocket 170 comprises a stretchy material, such as a Spandex® or Lycra® material. In some embodiments, nose pocket 170 comprises a material having a thickness that is less than the thickness of the remaining material of strap 140. In some embodiments, nose pocket 170 comprises excess material such that nose pocket is contoured into the general shape of a nose.

Smells and scents associated with commercial travel can be unpleasant. Further, some travelers experience anxiety and nervousness while traveling. Thus, in some embodiments nose pocket 170 may further comprise a scent, such as a scent strip that is inserted into nose pocket 170. The scent strip is located near the user's nostrils to provide an aroma therapy to the user. For example, a scent strip may comprise one or more relaxation scents or fragrances. In some embodiments, a scent strip may comprise a pleasant aroma to add comfort to the user while using the device 200. In some embodiments, nose pocket 170 comprises an absorbent material configured to receive a liquid scent, such as an essential oil.

In some embodiments, nose pocket 170 may comprise a removable air filter, such as a respirator. In some embodiments, nose pocket 170 may comprise a mount configured to receive an air filter. In some embodiments, a portion of nose pocket 170 may be removable or interchangeable with an air filter or a mount for selectively securing an air filter.

Figure 6A:
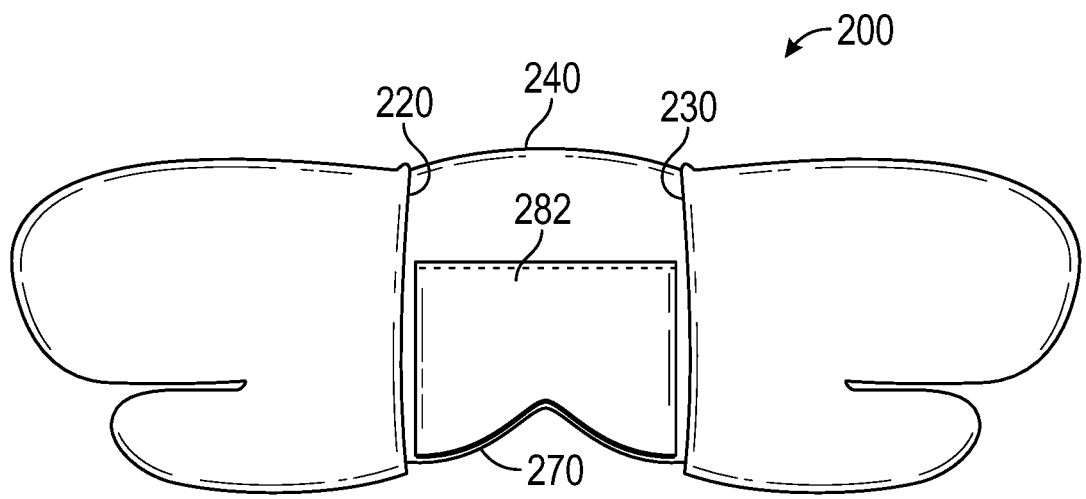
FIG. 6A is a front view of a head support device having an eye flap in a closed position in accordance with a representative embodiment of the present invention.
Figure 6B:
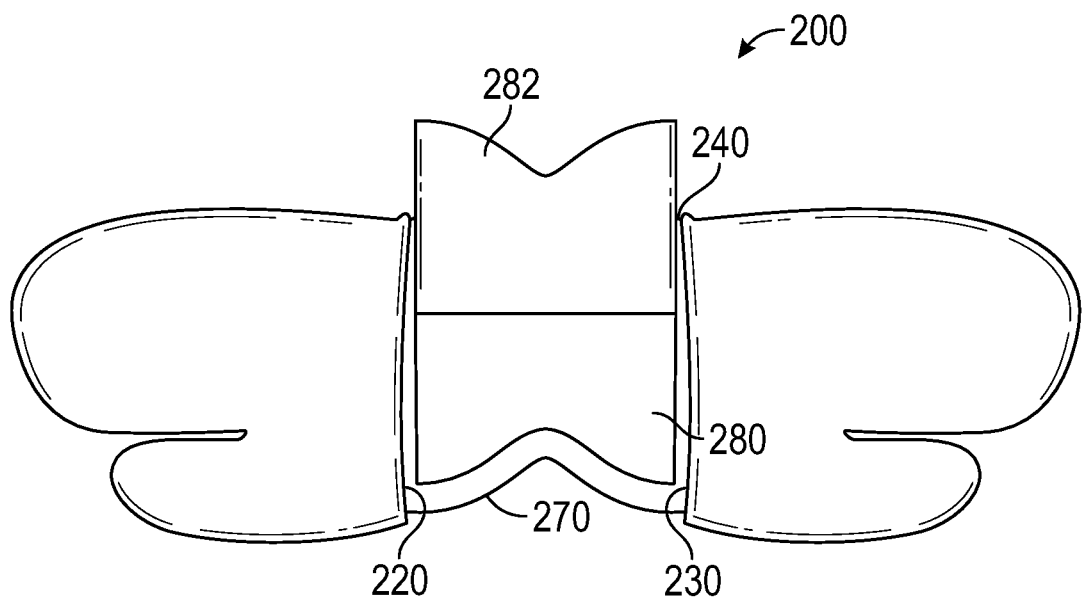
FIG. 6B is a front view of a head support device having an eye flap in an open position in accordance with a representative embodiment of the present invention.
Figure 6C:
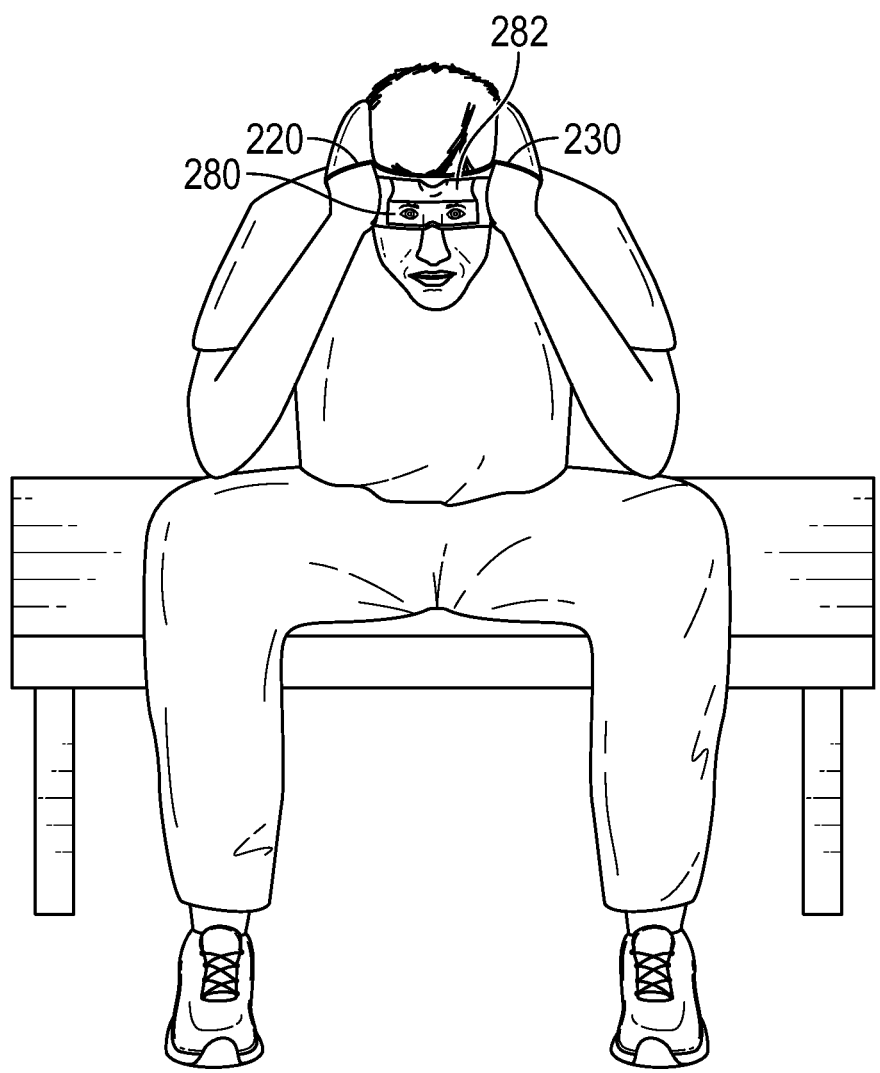
FIG. 6C is a front view representation of a user in a seated, hunched-over position, wherein the user's hands are interconnected via the head support device of FIGS. 6A and 6B, wherein the eye flap is in an open position.

Referring now to FIGS. 6A and 6B, in some embodiments a head support device 200 is provided having a nose pocket 270 comprising a wedged cutout configured to rest on top of the bridge of the user's nose. Device 200 may further comprise an eye window 280 that may be covered by a flap 282. Flap 282 may be configured to selectively cover eye window 280, such that the user may open the eye window 280 to facilitate viewing activities while wearing device 200, such as reading a book or watching a movie. In some embodiments, flap 282 is maintained in an open or closed position by a fastener, such as a hook and loop fastener. In some embodiments, eye window 280 may comprise a video display. In some embodiments, the video display is removably coupled to eye window 280.

Alternatively, the head support devices of the present invention may be positioned under the chin and/or across the mouth area for support. This alternative orientation allows the user to view entertainment or reading material of their choice while wearing the device.

Figure 7:
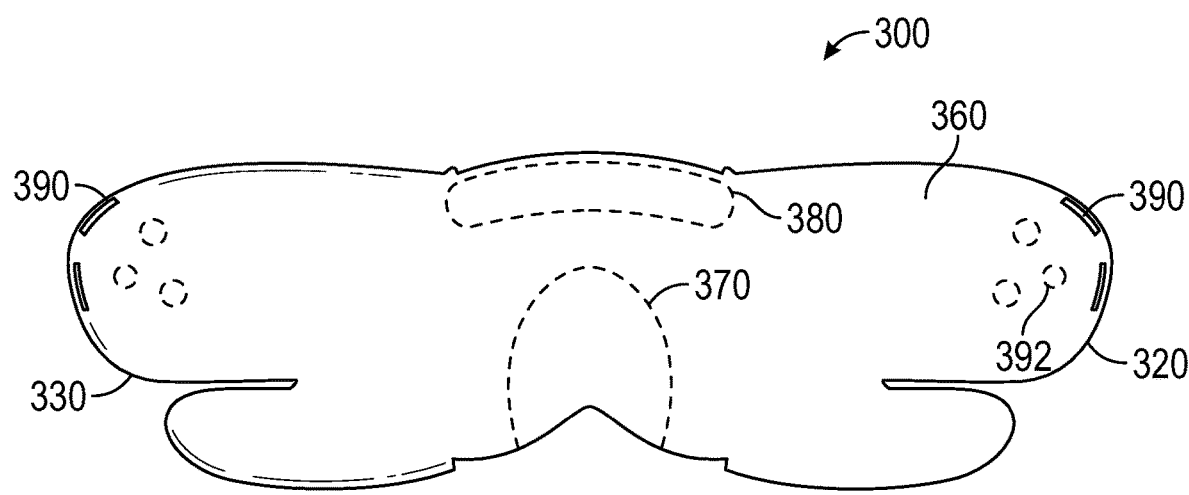
FIG. 7 is a rear view of a head support device having various comfort features in accordance with one or more representative embodiments of the present invention.

Referring now to FIG. 7, a head support device 300 may comprise various features to further accommodate a user's comfort when wearing the device. In some embodiments, device 300 further comprises a comfort pad 380 positioned so as to be located on, or at least in contact with the user's face, and preferably the user's forehead when the device is worn. Accordingly, comfort pad 380 may include a variety of shapes, sizes and configurations, as well as a variety of materials. Comfort pad 380 may comprise various functions to improve the user's experience in using the device. For example, in one embodiment comfort pad 380 comprising a cooling gel. In one embodiment, comfort pad 380 comprises additional padding material. In one embodiment, comfort pad 380 comprises therapeutic magnets. In one embodiment, comfort pad 380 comprises a reading light. In some embodiments, comfort pad 380 comprises an absorbent and/or moisture wicking material. In some embodiments, comfort pad 380 is selectively attached to palm side 360, such as by a hook and loop fastener, magnets, or mechanical friction.

Head support device 300 further comprises vents 390 to help regulate the temperature of the user's hands while inserted within hand apertures 320 and 330. In some embodiments, vents 390 are openings through which one or more controls are accessed through the material of device 300. For example, in some embodiments device 300 may comprise an A/V source control, such as a button, that is located within aperture 330 and accessible via vent or opening 390. In some embodiments, an A/V source control is at least one of a volume control, an input select, a toggle switch, an enter button, a joystick, a power button, or the like. In some embodiments, vents 390 comprise buttons or other surfaces or electrical components of device 300.

In some embodiments, device 300 further comprises openings 392 which are located on the palm side 370 of device 300, wherein said openings 392 provide a pathway through the material of device 300. In some embodiments, opening 392 comprise one or more physical pathways through which sound can travel to permit a user to listen to their headphones while holding their headphones with their hands, and specifically with their fingers and/or palm while positioned in apertures 320 and 330. In some embodiments, openings 392 comprise a physical pathway to facilitate venting to regulate the temperature of the user's hands, and specifically the user's palms while wearing device 300. In some embodiments, openings 392 further comprise a venting, filtering or backing material configured to prevent the user's fingers from inadvertently extending through, or otherwise getting caught on openings 392 during use. Non-limiting examples of venting, filtering, or backing materials may include a mesh material, a foam material, a sponge material, a netted material, a knit material, a low density material, or the like. In some embodiments, the backhand side further comprises one or more vents to facilitate venting to regulate the temperature of the user's hands during use of device 300.

In some embodiments, apertures 320 and 330 are lined with an additional material. For example, in some embodiments apertures 320 and 330 are lined with temperature regulating material, such as a material that removes heat from the user's hands, or a material that retains heat from the user's hands within apertures 320 and 330. In some embodiments, apertures 320 and 330 are lined with a moisture wicking material. In some embodiments, apertures 320 and 330 are lined with a scented material, such as a material that is infused with or otherwise treated with a scent, such as an essential oil.

Figure 8:
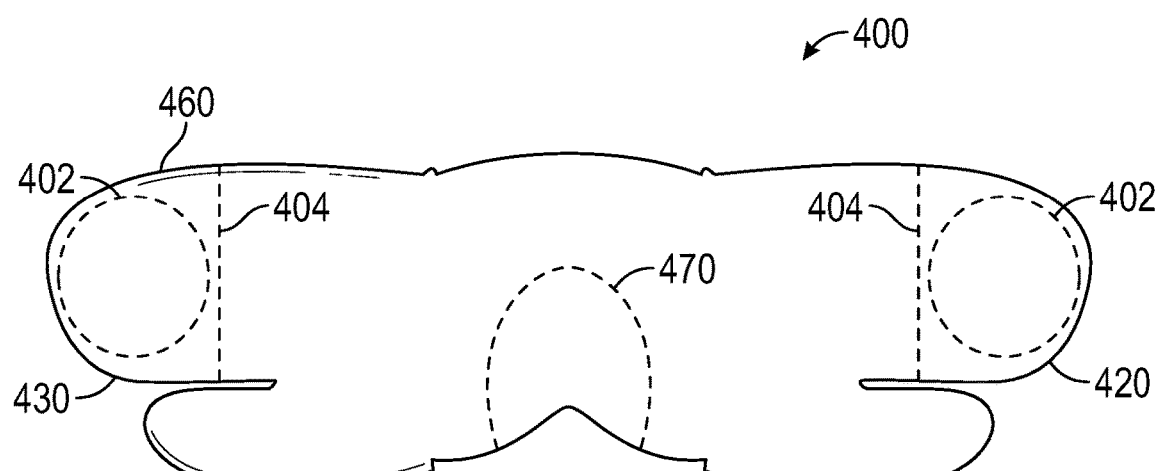
FIG. 8 is a rear view of a head support device having integrated headphone speakers in accordance with a representative embodiment of the present invention.

Referring now to FIG. 8, an alternative embodiment of the present invention is show as head support device 400. Some embodiments of the present invention further comprise headphones 402. In one embodiment, headphones 402 comprise wireless headphones, such as Bluetooth® headphones. In some embodiments, headphones 402 are rechargeable. In some embodiments, device 400 comprises pockets 404 that are sewn into or otherwise provided in opposite distal ends of hand apertures 420 and 430, wherein said pockets are configured to removably receive headphones 402, such as slim speakers. The headphone speakers 402 are oriented so as to face inward, or towards the user when the device is worn, thereby allowing the user to position the speakers over their ears. In some embodiments, controls for the headphone speakers are located on the opposite side of the actual speaker and accessible by the user while the user's hands are positioned within first and second hand apertures 420 and 430. This will allow the user to connect their device and listen to several different types of entertainment or answer a call without needing to remove their hands from the device 400.

Some embodiments incorporate additional useful features. For example, in some embodiments device 400 comprises finger controls for the volume in one hand aperture 420, and cursor controls in the opposite hand aperture 430, which is also configured to be controlled by the user's fingers. The cursor control enables the user to control their device, such as select a desired media (i.e., song, movie, application, etc.), without requiring the user to disengage from the device 400. Thus, the user may maintain their forward relaxation position (i.e., both hands supporting the user's head) while still having full control of their device, such as playing a game, scrolling through a virtual book, typing an email/text, or skipping or rewinding a movie. In various embodiments, moisture sensitive components may be removed to facilitate washing of the device.

Figure 9A:
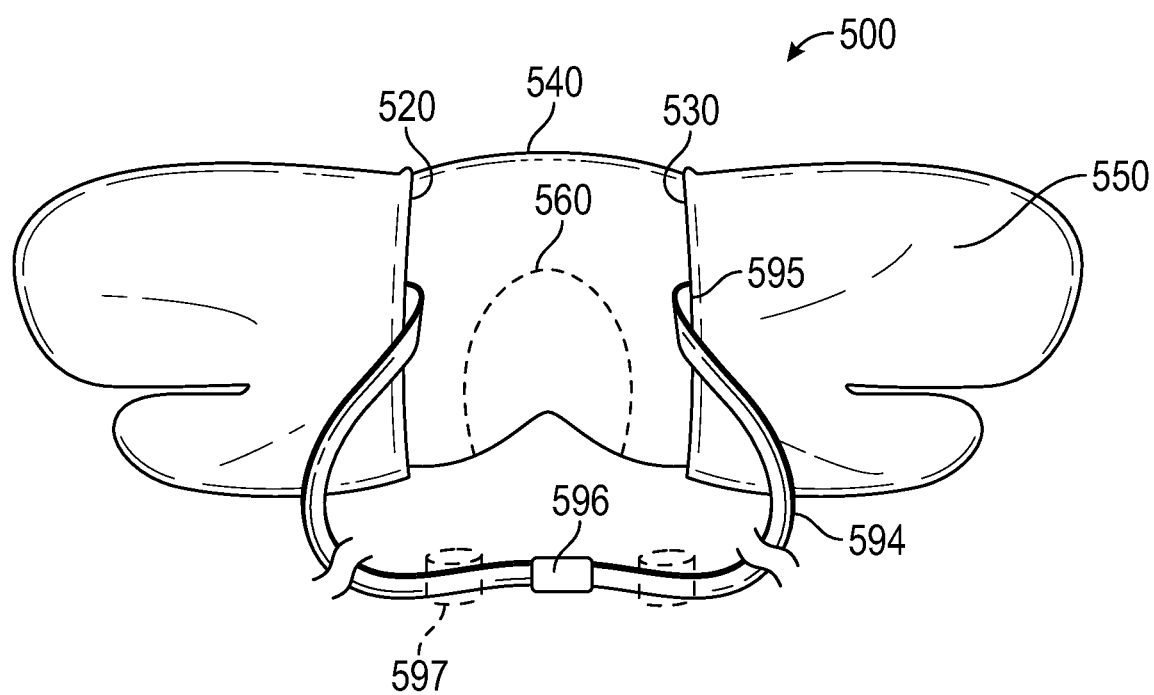
FIG. 9A is a front view of a head support device having an integrated restraint in accordance with a representative embodiment of the present invention.
Figure 9B:
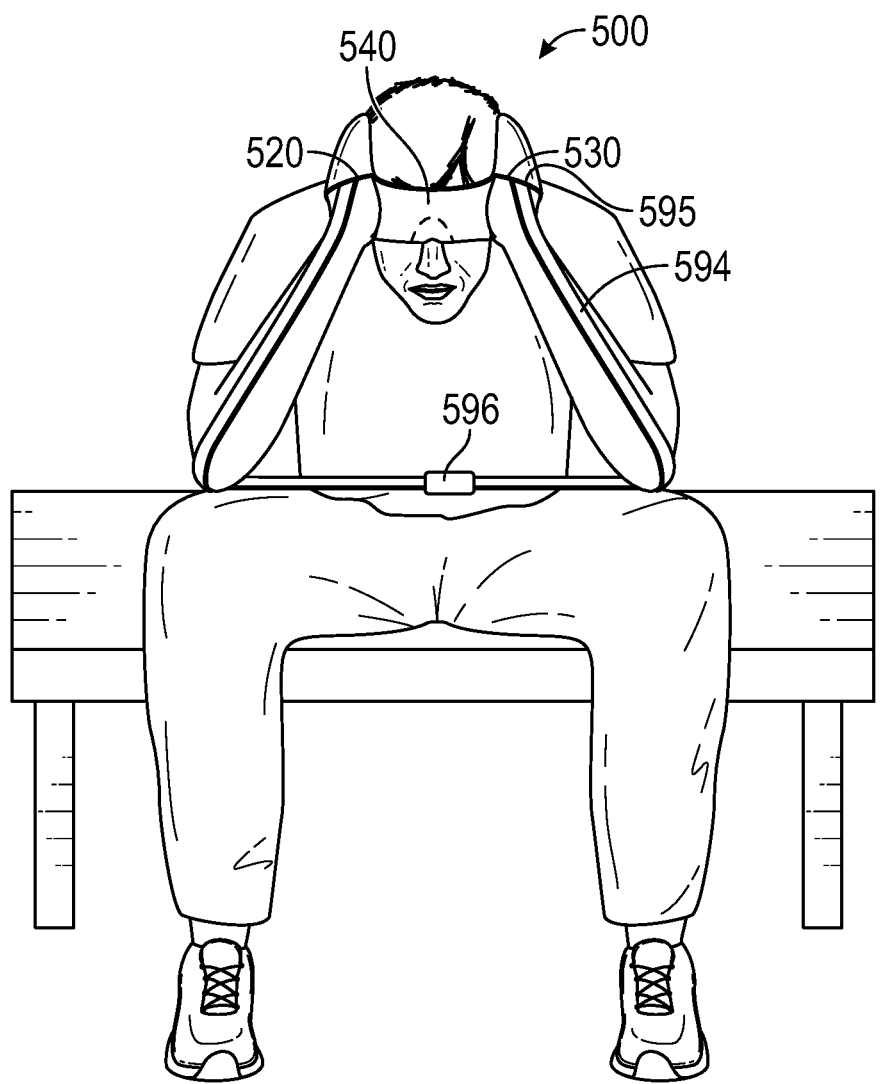
FIG. 9B is a front view representation of a user in a seated, hunched-over position, wherein the user's hands are interconnected, and the user's elbows are restrained via the head support device of FIG. 9A.
Figure 9C:
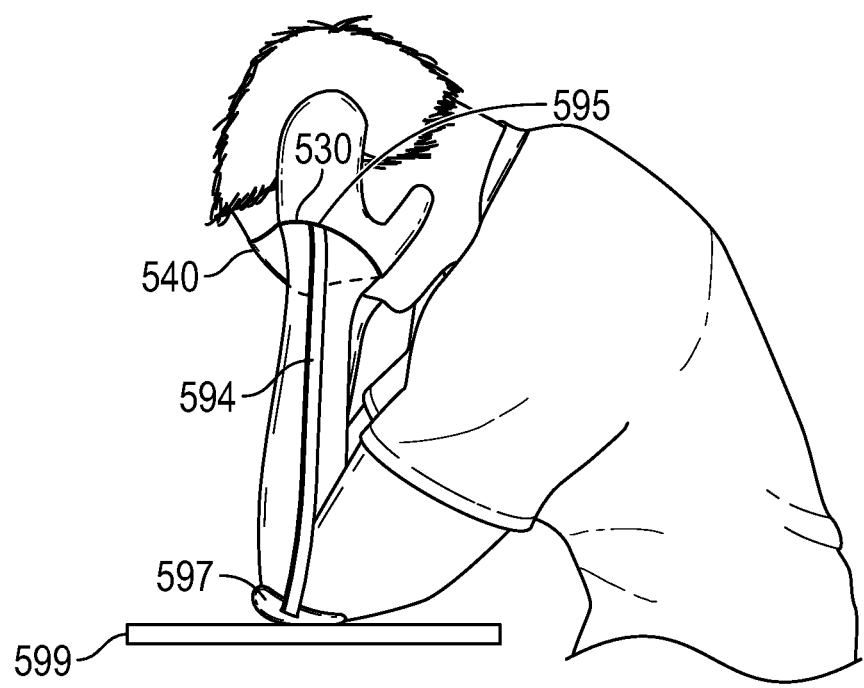
FIG. 9C is a side view representation of a user in a seated, sleeping position wherein the user's hands are interconnected, and the user's elbows are restrained via the head support device of FIG. 9A.

Any of the embodiments of the present invention may further comprise a restraint configured to hold the user's arms in a desired position while using the head support device. Referring now to FIGS. 9A-9C, head support device 500 is shown having an integrated restraint 594. Restraint 594 may comprise any materials and features compatible for use in the present invention. In some embodiments, restraint 594 comprises a nylon webbing belt or strap having ends 595 that are coupled to, and extend outwardly from hand apertures 520 and 530. In some instances, ends 595 are selectively coupled to hand apertures 520 and 530, such that restraint 592 may be selectively removed or added to head support device 500. Restraint 594 may comprise any length and width compatible for use in the present invention. In some embodiments, restraint 594 comprise a width (constant or varying) of from approximately 2.5 cm to approximately 8.0 cm. Restraint 594 may comprise a buckle 596 dividing restraint 594 into two or more sections. Non-limiting examples of compatible buckles include side-release buckles, ladderlock buckles, cam buckles, D-ring buckles, parachute buckles, and the like. In some instances, restraint 594 comprises a plurality of notches or holes for engaging a buckle 596 at desired lengths of restraint 594.

Restraint 594 may further include padding or cushion material 597. Padding material 597 is generally provided for use between the user's arms and a hard surface 599, such as between the user's elbows and a table 599, as shown in FIG. 9C. Padding material 597 may comprise a singular piece having an elongated length sufficient for simultaneous contact and support of user's elbows, or may comprise two or more pieces placed at positions corresponding to a desired surface of the user's arms, such as the user's elbows. Padding material 597 may be threaded onto restraint 594 such that padding material may translate over the length of restraint 594. In some instances, padding material 597 is secured at, or securable to, a desired position on restraint 594.

In use, restraint 594 is positioned in proximity to the back surface of the user's hands at end 595, and extends downwardly therefrom along the top surface of the user's forearm. However, embodiments are contemplated wherein restraint 594 is attached to the hand opening on the palm surface, such that restraint 594 contacts the user's wrist and wraps around the top or bottom surfaces of the user's forearms, and then to the user's elbows. The user's elbows contact restraint 594 at a position where one or more surfaces of restraint 594 contacts the surface supporting the user's elbows (e.g., hard surface 599, or the top surface of the user's thighs), such that restraint 594 is interposed between the user's elbows and the supporting surface. In some embodiments, padding material 597 is further interposed between restraint 594 and the user's elbows. The length of restraint 594 is further adjusted via buckle 596 to provide an ergonomic fit for the user. In some instances, the length of restraint 594 is selected such that a distance between the user's elbows is greater than a distance between the user's hands when device 500 is worn and used.

Figure 10A:
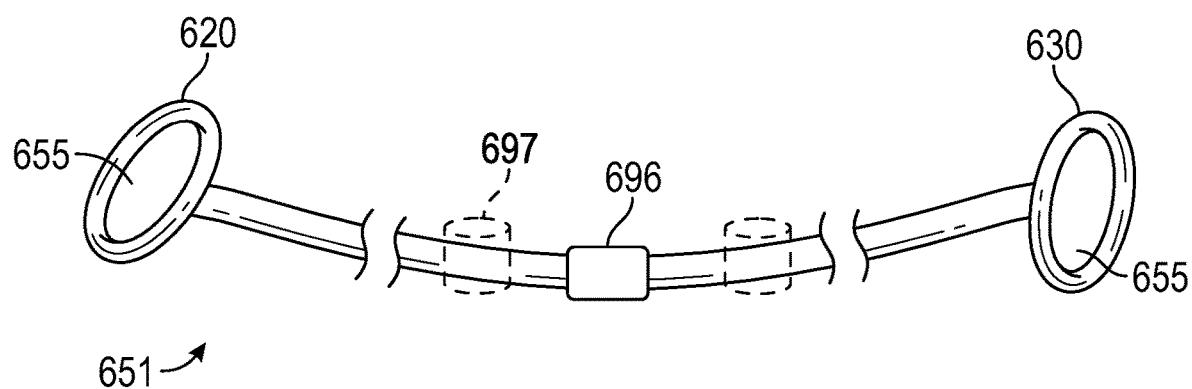
FIG. 10A is a front view of a separate restraint for use with various head support devices in accordance with various representative embodiments of the present invention.
Figure 10B:
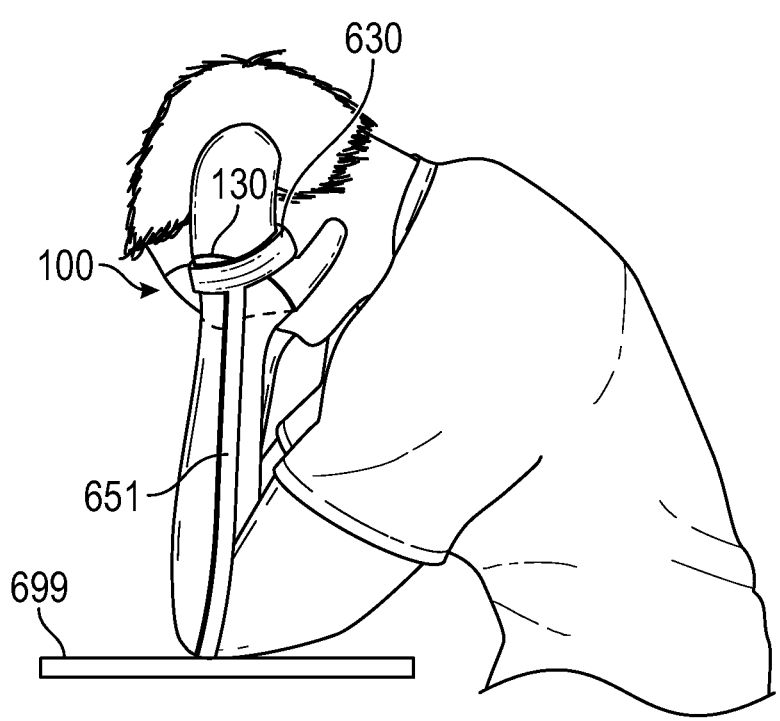
FIG. 10B is a side view representation of a user in a seated, sleeping position wherein the users hands are interconnected via a head support device, and the user's elbows are restrained via the separate restraint of FIG. 10A.

Referring now to FIGS. 10A and 10B, any compatible head support device (shown as 100, however may also include any of head support devices 200, 300 and/or 400 disclosed herein) may be used with a separate restraint 651. Restraint 651 may comprise any materials and features compatible for use in the present invention. In some embodiments, restraint 651 comprises a nylon webbing belt or strap having hand apertures 620 and 630, each having an opening 655 for receiving the user's hand, and in particular the user's index, middle, ring, and little fingers (i.e., phalanges), such that the looped ends 653 are placed around the user's metacarpal bones, or middle portion of the user's hand. In some instances, hand apertures 620, 630 each comprise two or more smaller loops (i.e., finger loops), each loop configured to receive individual phalanges of the user.

Restraint 651 may comprise any length and width compatible for use in the present invention. In some embodiments, restraint 651 comprise a width (constant or varying) of from approximately 2.5 cm to approximately 8.0 cm. Restraint 651 may comprise a buckle 696 dividing restraint 651 into two or more sections. Non-limiting examples of compatible buckles include side-release buckles, ladderlock buckles, cam buckles, D-ring buckles, parachute buckles, and the like. In some instances, restraint 651 comprises a plurality of notches or holes for engaging a buckle 696 at desired lengths of restraint 651.

Restraint 651 may further include padding or cushion material 697. Padding material 697 is generally provided for use between the user's arms and a hard surface 699, such as between the user's elbows and a table 5699, as shown in FIG. 10B. Padding material 697 may comprise a singular piece having an elongated length sufficient for simultaneous contact and support of user's elbows, or may comprise two or more pieces placed at positions corresponding to a desired surface of the user's arms, such as the user's elbows. Padding material 697 may be threaded onto restraint 694 such that padding material may translate over the length of restraint 651. In some instances, padding material 697 is secured at, or securable to, a desired position on restraint 651.

In use, hand apertures 620, 630 of restraint 651 are placed over the user's hands while the user's hands are positioned within hand apertures 120, 130 of head support device 100. Accordingly, head support device 100 may be used with or without restraint 651. Hand apertures 620, 630 are oriented such that when the user's hands or fingers are inserted therein, restraint 651 is positioned in proximity to the back surface of the user's hands at end 595, and extends downwardly therefrom along the top surface of the user's forearm. However, embodiments are contemplated wherein restraint 651 is positioned such that the intersection of hand apertures 620, 630 and restraint 651 contacts the user's wrist and wraps around the top or bottom surfaces of the user's forearms, and then to the user's elbows. The user's elbows contact restraint 651 at a position where one or more surfaces of restraint 651 contacts the surface supporting the user's elbows (e.g., hard surface 699, or the top surface of the user's thighs), such that restraint 651 is interposed between the user's elbows and the supporting surface. In some embodiments, padding material 697 is further interposed between restraint 651 and the user's elbows. The length of restraint 651 is further adjusted via buckle 696 to provide an ergonomic fit for the user. In some instances, the length of restraint 651 is selected such that a distance between the user's elbows is greater than a distance between the user's hands when head support device 100 is worn and used.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A head support device, comprising:
    a strap having a middle, a first distal end, and a second distal end, said middle having an upper portion configured for placement over a user's eyes and brow, and a lower portion configured for placement over a user's nose;
    a right hand aperture fixedly connected to the first distal end and comprising an opening defining a first receptacle comprising a right thumb pocket and a right finger pocket, wherein said right thumb pocket is distinct from said right finger pocket;
    a left hand aperture fixedly connected to the second distal end and comprising an opening said second hand aperture having a single second opening defining a second receptacle having a left thumb pocket and a left finger pocket, wherein said left thumb pocket is distinct from said left finger pocket; and
    a nose pocket positioned in the lower portion of the middle of the strap and comprising an indent formed in a lower edge of the strap and in horizontal alignment with the left and right thumb pockets.

2. The device of claim 1, wherein at least one of the right hand aperture and the left hand aperture is a mitten.

3. The device of claim 1, wherein at least one of the right hand aperture and the left hand aperture is a glove.

4. The device of claim 1, wherein the strap comprises a length that is from 3 inches to 8 inches.

5. The device of claim 1, further comprising an eye window.

6. The device of claim 1, further comprising a comfort pad.

7. The device of claim 1, further comprising venting.

8. The device of claim 1, further comprising speakers.

9. The device of claim 8, wherein the speakers are wireless.

10. A method for maintaining a seated sleeping position, said method comprising:
    placing a first hand in the first receptacle of the right hand aperture of the device of claim 1 such that the fingers of the first hand are positioned in the right finger pocket and the thumb is positioned in the right thumb pocket;
    placing a second hand in the first receptacle of the left hand aperture of said device such that the finger of the second hand are positioned in the left finger pocket and the thumb is positioned in the left thumb pocket;
    resting the strap portion of said device against a user's face such that the user's nose is located in the nose pocket and the user's palms and fingers are oriented against the sides of the user's head, such that the user's thumbs are oriented below the user's fingers; and
    assuming a seated sleeping position by first sitting, and then resting the elbows of the user atop a surface in front of the user, whereby the weight of the user's head is transferred to the surface via said device and the user's forearms.

* * * * *